United States Patent [19]

Osamu et al.

[11] 4,123,443

[45] Oct. 31, 1978

[54] PROCESS FOR THE PREPARATION OF BROMOACETIC ACID AND ESTERS THEREOF

[75] Inventors: Umekawa Osamu, Takatsuki; Takemori Koji, Osaka; Katayama Sakae, Kobe, all of Japan

[73] Assignee: Katayama Chemical Works Co., Ltd., Osaka, Japan

[21] Appl. No.: 883,519

[22] Filed: Mar. 6, 1978

Related U.S. Application Data

[63] Continuation of Ser. No. 721,792, Sep. 9, 1976, abandoned.

[30] Foreign Application Priority Data

Sep. 16, 1975 [JP] Japan ................................. 50-112381
Sep. 20, 1975 [JP] Japan ................................. 50-113897

[51] Int. Cl.$^2$ ...................... C07C 53/16; C07C 69/63
[52] U.S. Cl. .................................. 260/347.4; 560/226; 560/228; 560/229; 560/230; 562/602
[58] Field of Search ........................ 260/539 A, 347.4; 560/226, 228, 229, 230

[56] References Cited

U.S. PATENT DOCUMENTS 2,876,255 3/1959 Johnston .............................. 260/487
3,130,222 4/1964 Asadorian et al. .............. 260/539 A

*Primary Examiner*—Jane S. Myers
*Attorney, Agent, or Firm*—Hubbell, Cohen, Steefel & Gross

[57] ABSTRACT

New economically valuable and convenient methods for preparing bromoacetic acid and its esters from chloroacetic acid are disclosed.

10 Claims, No Drawings

PROCESS FOR THE PREPARATION OF BROMOACETIC ACID AND ESTERS THEREOF

This is a continuation of application Ser. No. 721,792, filed Sept. 9, 1976.

BACKGROUND OF THE INVENTION

BACKGROUND OF THE INVENTION

1. Field of the Invention

This invention relates to a process for the preparation of bromoacetic acid and esters thereof.

2. Description of the Prior Art

Some of bromoacetic acid esters have been broadly used as non-medical bacteriocides which show remarkable antibacterial activities. A generally well-known synthetic method of bromoacetic acid esters is that acetic acid is reacted with bromine in the mixed solvent of acetic anhydride and pyridine and the resultant is esterified, as reported in Organic Synthesis, Collective Volume 3, p. 381 (1943), Paragraph of Synthesis of ethyl bromoacetate.

On the other hand, as synthetic methods of bromoacetic acid there have been known the reaction of chloroacetic acid and hydrogen bromide (Ber. 9, 561 (1876)), the method of bubbling gaseous hydrogen bromide into a solution of chloroacetic acid ester and hydrogen bromide (W. German Provisional Publication Specification No. 2,151,563 (1973)) and the method from chloroacetic acid in a similar way with said Specification No. 2,151,565 (U.S. Pat. No. 3,130,222 (1964. Also, the reaction of acetic acid and bromine in the mixed solvent of acetic acid anhydride and pyridine as described in the above Organic Synthesis has been known as a general method for preparing bromoacetic acid.

As represented by these prior publications, bromoacetic acid esters could be prepared by firstly reacting acetic acid or chloroacetic acid with a brominating agent to prepare bromoacetic acid, then isolating it, and subjecting the product to a conventional esterifying method, i.e., such as esterifying bromoacetic acid with an alcohol in the presence of a catalyst such as sulfuric acid.

However, such known methods are disadvantageous on practices in an industrial scale, because their procedures are comparatively laborious, and in addition their yields are not satisfactory and their reaction times are sometimes long.

It is an object of the invention to prepare bromoacetic acid as well as its esters, by a compact procedure and with high yields using raw materials of cheap prices.

DETAILED DESCRIPTION

Thus, according to the invention, there is provided a process for the preparation of bromoacetic acid esters which comprises adding conc.- sulfuric acid gradually into a mixture of chloroacetic acid, an alkali metal or ammonium bromide, an alcohol, water and an organic solvent which can form an azeotrope, so as to maintain the mixture at a temperature from about 40° C to about 70° C, heating it to complete the reactions while removing water and then isolating a bromoacetic acid ester from the organic layer. Alternatively, the process comprises adding conc.- sulfuric acid gradually into an aqueous solution of chloroacetic acid and an alkali metal or ammonium bromide, so as to maintain the aqueous solution at a temperature from about 40° C to about 70° C, and (b) adding an organic solvent which can form an azeotrope into the reaction mixture, heating it while removing water and further heating the resultant after the addition of an alcohol; or (b') adding both of an organic solvent which can form an azeotrope and an alcohol into the reaction mixture and heating it while removing water, and then (c) isolating a bromoacetic acid ester from the organic layer. If the addition of the alcohol and/or the organic solvent are omitted in this alternative process, bromoacetic acid can be obtained.

A main feature of the methods according to the present invention is that the procedure is very compact and the reactions involved can be conducted in one reaction vessel. Another feature is that an advantage on cost can enjoy, because chloroacetic acid and bromine salt used for the raw materials are commercially available on reasonable prices, the period required for the reactions is comparatively short and yields are high. A further feature is to able to prepare either bromoacetic acid or its esters upon request. The reaction procedures and conditions of the method according to the invention are explained as below.

The production of bromoacetic acid esters from chloroacetic acid can be divided into two reactions of bromination and esterification. Although the invention has a big feature in carrying out these two steps of reactions with an unit procedure, it can be divided, from the viewpoint of reactions, into the method of completing firstly the bromination and then carrying out the esterification and the method of carrying out the esterification at an stage that the bromination proceeded in some extent.

The procedure (1) which belongs to the former method, is to add conc.- sulfuric acid into a mixture of chloroacetic acid, an alkali metal or ammonium bromide, an alcohol, water and an organic solvent which can form an azeotrope, and complete the reaction removing water under heating.

The procedure (2) which belongs to the latter method, is to add conc.— sulfuric acid into a mixture of chloroacetic acid and an alkali metal ammonium bromide, then heat the reaction mixture after the addition of an organic solvent which can form an azeotrope, to complete the bromination while removing water and further add an alcohol into the reaction mixture and heat it. The further procedure (3) belonging to the latter method is to add conc.— sulfuric acid into an aqueous solution of chloroacetic acid and an alkali metal or ammonium bromide and heating the mixture after the addition of both of an organic solvent which can form an azeotrope and an alcohol, while removing water.

The alkali metal bromides used for the invention include potassium bromide, sodium bromide and the like. Such bromides are not needed to be high grade of purity and may be ones which are readily available. For example, they may be sufficient to some compounds.

The ratio of chloroacetic acid, a bromine salt and conc.- sulfuric acid may be preferably in the range of 1 : 1 : 1 to 1 : 1.5 : 1.5, usually 1 : 1.3 : 1.1 ~ 1.3. The sulfuric acid is gradually dropped into a mixture in such extent that the temperature due to the exothermic reaction is kept below 70° C, preferably at 50° C ~ 60° C.

Sulfuric acid is preferred to be in the concentration of over about 95%. What increases an amount of water as the reaction medium serves to eliminate a risk of exceeding the intended temperature, but is not advantageous because it requires a long time for completion of the reaction and for dehydration procedure. Accordingly, the amount of water in the reaction mixture is preferably less 200 ml per one molecular amount of chloroacetic acid, usually about 100 ml.

The alcohols used in the method of the invention may be mono-, di- and poly-alcohols which are generally used as the materials of esterification. There may be mentioned: aliphatic saturated alcohols such as hexyl alcohol, lauryl alcohol, ethylene glycol, 1,4-butandiol, glycerol or the like; aliphatic halogeno alcohols such as 2-chloropropanol, 1-chloro-3-bromo-2-methylpropanol, 2,3-dichloropropanol or the like; aliphatic nitro alcohols such as 2-nitro-2-methylpropanol or the like; alicyclic alcohols such as cyclohexanol, 2-ethylcyclohexanol, cis-1,2-cyclohexandiol, 2-cyclohexanol, 2-chlorocyclohexanol or the like; aromatic saturated alcohol such as benzyl alcohol, p-methoxybenzyl alcohol, cinnamyl alcohol, p-chlorobenzyl alcohol or the like; heterocyclic alcohol such as furfuryl alcohol, tetrahydrofurfuryl alcohol or the like; glycol monoalkylether such as ethylene glycol monobutylether, propylene glycol monoethylether or the like.

Any of the above mentioned procedures may be arbitrarily usable for these alcohols, but yields will be depended on the kind of the alcohol employed. The alcohols suitable for the procedures (1 and (2) may be the aliphatic halogeno alcohols and the aliphatic nitro alcohols. Also the procedure (2) may be applicable for all kinds of the alcohols.

The organic solvents which can form an azeotrope means organic solvents which can be azeotropically distilled with water. The preferred examples are tetrachloroethylene (perclene), benzene, toluene, xylene or the like. The most preferred one is tetrachloroethylene.

At the stage of the completion of sulfuric acid addition, the reaction mixture is preferably stirred for a short time such as 30 minutes or an hour at about 55° C. Then, to proceed further the bromination, the mixture wherein the organic solvent, or the organic solvent and the alcohol are involved is heated, while water in the mixture is gradually removed. The esterification when the alcohol presented will simultaneously proceed.

In case of the procedure (2), i.e., the method of conducting the esterification after the dehydration treatment, it is necessary to take a procedure to take off the resulting water.

After the completion of the reactions, bromoacetic acid esters may be obtained, e.g., by filtering off the resulted hydrogen sulfate and distilling off the solvent used. Thus bromoacetic acid esters are obtained with high yields and purities.

Further, when bromoacetic acid needed, it can be isolated in the course of the procedures (2) and (3). That is, to an aqueous solution of chloroacetic acid and an alkali metal or ammonium bromide is gradually added conc.-sulfuric acid so as to maintain the mixture at a temperature from about 40° C to about 70° C and the reaction mixture after stirring for a short time is heated while removing water, by which the bromination will be completed and the simultaneous isolation of bromoacetic acid can be achieved, when taken for an azeotropic distillation with the organic solvent as mentioned above or a distillation under reduced pressure or blowing an inert gas such as air or nitrogen gas through the mixture.

The following examples are given for the purpose of illustrating the invention.

EXAMPLE 1

Preparation of 2,3-Dichloropropyl Bromoacetate 94.5g (1 mol) of chloroacetic acid, 154.7g of potassium bromide and 129g (1 mol) of 2,3-dichloro-1-propanol were put into a 1 liter four necked flask equipped with a stirrer, a thermometer, a reflux condenser and a dropping funnel. To the mixture were added 100 ml of water as a reaction medium and 200g of toluene as an azeotropic solvent and stirred vigorously. Then 127.5g (1.3 mol) of c.-sulfuric acid were added dropwise to the solution over the course of an hour, maintaining the mixture at 55° C ± 5° C. After the completion of addition, the solution was heated to about 100° – 120° C and refluxed for an hour. Then a receiver was attached to reflux condenser and water was removed by azeotropic distillation with toluene from the reaction mixture. After the completion of this procedure, the produced crystals of potassium hydrogen sulfate were filtered off to yield a solution of toluene containing 2,3-dichloropropyl bromoacetate, which can be industrially used as it is. If needed, toluene was removed from the filtrate followed by distillating the residue to give 239.5g of 2,3-dichloropropyl bromoacetate of bp. 123° ~124° C (3 mmHg) as a colorless and clear liquid (95.8% of theory). $n_D^{25} = 1.5021$, $D_4^{20} = 1.6932$. 176.6g (99.8% of theory) of potassium hydrogen sulfate was isolated.

EXAMPLE 2

Preparation of 2-nitro-3-bromo-n-butyl bromoacetate 94.5g (1 mol) of chloroacetic acid, 132.6g (1.3 mol) of sodium bromide, 198g (1 mol) of 2-nitro-3-bromo-n-butanol, 127.4g (1.3 mol) of c.-sulfuric acid, 100 ml of water and 200g of toluene were used and treated in a similar way as described in Example 1. The reaction mixture was heated for 1.5 hrs. in an oil bath, during which water was removed by azeotropic distillation with toluene. 294.7g (92.4% of theory) of 2-nitro-3-bromo-n-butyl bromoacetate. Bp. 130° C/3mmHg, $n_D^{20} = 1.5060$, $D_4^{20} = 1.7876$. 162.6g (98.4%) of sodium hydrogen sulfate was isolated.

EXAMPLE 3

Preparation of lauryl bromoacetate 94.5g (1 mol) of chloroacetic acid, 142.8g (1.2 mol) of potassium bromide and 100 ml of water (as a reaction medium) were put into a 1 liter four necked flask equipped with a stirrer, a thermometer, a dropping funnel and a reflux condenser attached with a receiver. Then 117.6g (1.2 mol) of c.-sulfuric acid were added droppwise to the mixture at a constant rate over the course of an hour. After the droppwise addition, stirring was continued for an hour at 65° C in a water bath. Then 200g of toluene were added to the reaction system, during which water was removed by azeotropic distillation.

To the mixture were added 186g (1 mol) of laurylalcohol and refluxed for 2 hrs at 115° ~ 120° C, while removing the resultant water by azeotropic distillation with toluene. After the completion of the procedure, the resultant crystals of potassium hydrogen sulfate were filtrated to give a toluene solution containing lauryl bromoacetate, which was sufficient to use industrially as it is. But if needed, toluene was removed from the filtrate followed by distillating the residue to give 301.2g (98%) of lauryl bromoacetate of 151° ~ 153° C (3 mmHg) as a colorless and clear liquid. $n_D^{20} = 1.4605$, $D_4^{20} = 1.111$. 162.9g (99.8%) of potassium hydrogen sulfate was isolated.

EXAMPLE 4

Preparation of 1,2-bis-(bromoacetoxy) ethane 94.5g (1 mol) of chloroacetic acid, 132.6g (1.3 mol) of sodium bromide, 127.4g (1.3 mol) of sulfuric acid, 100 ml of water, 200g of toluene and 31g (0.5 mol) of ethylene glycol were used and treated in a similar way as described in Example 3. 129.5g (85.2% of theory) of 1,2-bis-(bromoacetoxy) ethane were obtained. Bp = 144 ~ 145° C/2 mmHg, $n_D^{20} = 1.5077$, $D_4^{20} = 1.8333$. 163.4g of sodium hydrogen sulfate was isolated (98.9%).

EXAMPLE 5

Preparation of propargyl bromoacetate 47.3g (0.5 mol) of chloroacetic acid, 77.4g (0.65 mol) of potassium bromide, 63.7g (0.65 mol) of c.-sulfuric acid, 500 ml of water, 100g of toluene and 28.1g (0.5 mol) of propargyl alcohol were used and treated in a similar way as described in Example 3. After the dropwise addition of sulfuric acid, stirring was continued for an hour at 55° C in a water bath. Then water was removed by azeotropic distillation with toluene, by which 81.7g of propargyl bromoacetate were obtained. The yield was 92.3% of theory. Bp = 143° ~ 145° C/20 mmHg, $n_D^{20} = 1.4851$. 88g (99.4%) of potassium hydrogen sulfate was isolated.

EXAMPLE 6

Preparation of 1,4-bis-(bromoacetoxy)-2-butene 94.5g (1 mol) of chloroacetic acid, 154.7g (1.3 mol) of potassium bromide, 117.6g (1.2 mol) of c.-sulfuric acid, 150 ml of water, 200g of toluene and 44.1g (0.5 mol) of cis-2-butene-1,4-diol were used and treated in a similar way as described in Example 3. After the droppwise addition of sulfuric acid, stirring was continued for an hour at 70° C in a water bath. Then water was removed by azeotropic distillation with toluene, by which 137.6g of 1,4-bis-(bromoacetoxy-2-butene were obtained. The yield was 83.4% of theory. Bp. = 197° ~ 198° C/0.5 mmHg, $n_D^{20} = 1.5233$. 149.9g (98.3%) of potassium hydrogen sulfate was isolated.

EXAMPLE 7:

Preparation of cyclohexyl bromoacetate 94.5g (1 mol) of chloroacetic acid, 132.6g (1.3 mol) of sodium bromide, 127.4g (1.3 mol) of c.-sulfuric acid, 75 ml of water, 200g of toluene and 100.1g (1 mol) of cyclohexanol were used and treated in a similar way as described in Example 3. After the droppwise addition of sulfuric acid, stirring was continued for an hour at 55° C in a water bath. Water was removed by azeotropic distillation with toluene, by which 213.4g of cyclohexyl bromoacetate were obtained. The yield was 96.5% of theory. Bp. = 130° C/10 mmHg, $n_D^{25} = 1.4856$, $D_4^{20} = 1.3922$. 164.2g (99.4%) of sodium hydrogen sulfate was isolated.

EXAMPLE 8

Preparation of benzyl bromoacetate 94.5g (1 mol) of chloroacetic acid, 154.7g (1.3 mol) of potassium bromide, 127.4g (1.3 mol) of c.-sulfuric acid, 75 ml of water, 200g of toluene and 108g (1 mol) of benzylalcohol were used and treated in a similar way as described in Example 3. 214g (93.4% of theory) of benzyl bromoacetate were obtained. Bp. = 145° C/4 mmHg. 176.5g (99.7%) of potassium hydrogen sulfate was isolated.

EXAMPLE 9

Preparation of 2-n-butoxyethyl bromoacetate 94.5g (1 mol) of chloroacetic acid, 142.8g (1.2 mol) of potassium bromide, 117.6g (1.2 mol) of sulfuric acid, 75 ml of water, 200g of toluene and 118.1g (1 mol) of ethylene glycol butyl ether were used and treated in a similar way as described in Example 3. 225.1g (94.1% of theory) of 2-n-butoxyethyl bromoacetate were obtained. Bp. = 123° ~ 124° C/3 mmHg, $n_D^{25} = 1.4572$, $D_4^{20} = 1.6450$. 161.4g (98.9%) of potassium hydrogen sulfate was isolated.

EXAMPLE 10

Preparation of 1-chloro-2-propyl bromoacetate 94.5g (1 mol) of chloroacetic acid and 154.7g of potassium bromide were put into a 1 liter four necked flask equipped with a stirrer, a thermometer, a reflux condenser and a dropping funnel. To the mixture were added 100 ml of water as a reaction medium and stirred vigorously. Then 127.4g (1.3 mol) of c.— sulfuric acid were added droppwise over the course of an hour at a constant rate. During that time, the temperature of the reaction mixture rose to about 50° C. After the droppwise addition, stirring was continued for an hour at 55° C. Then 94.5g (1 mol) of 1-chloro-2-propanol and 200g of toluene were added to the reaction mixture, and refluxed for an hour at 100° ~ 110° C in an oil bath. A receiver was attached to a reflux condenser and water was removed from the reaction mixture by azeotropic distillation with toluene. Then the resultant crystals of potassium hydrogen sulfate were filtered off from the reaction mixture to give a toluene solution of 1-chloro-2-propyl bromoacetate, which was sufficient to use industrially as it is. But if needed, toluene was removed from the filtrate followed by distillating the residue to give 201.2g (93.4% of theory) of 1-chloro-2-propyl bromoacetate of bp 76° ~ 77° C (2 mmHg) as a colorless and clear liquid. $n_D^{25} = 1.4780$, $D_4^{20} = 1.5933$. 176.6g (99.8%) of potassium hydrogen sulfate was isolated.

EXAMPLE 11

Preparation of 2-nitro-3-bromo-n-butyl bromoacetate 94.5g (1 mol) of chloroacetic acid, 132.6g (1.3 mol) of sodium bromide, 127.4g (1.3 mol) of c.-sulfuric acid, 100 ml of water, 198g (1 mol) of 2-nitro-3-bromo-n-butanol and 200g of toluene were used and treated in a similar way as described in Example 10. 291.2g of 2-nitro-3-bromo-n-butyl bromoacetate were obtained (91.3% yield of theory). Bp 130° C/0.3 mmHg, $n_D^{20} = 1.5060$, $D_4^{20} = 1.7876$. 175g (98.9%) of potassium hydrogen sulfate was isolated.

EXAMPLE 12

Preparation of bromoacetic acid 94.5g (1 mol) of chloroacetic acid, 133.7g (1.3 mol) of sodium bromide were put into a 1 liter four necked flask with a stirrer, a thermometer, a reflux condenser and a dropping funnel, to which 100 ml of water was added and stirred vigorously. 127.5g (1.3 mol) of sulfuric acid was gradually dropped in the mixture, taking an hour and keeping at about 55° C. After the addition, the mixture was stirred for 2 hrs. 200g of toluene was added to the reaction mixture and heated in an oil bath to remove water by azeotropic distillation with toluene. After the completion of removal of water, the residue was filtered to remove crystals of sodium hydrogen sulfate. The resulted toluene solution containing bromoacetic acid was distilled to obtain 136g of bromoacetic acid of bp 91° ~ 92° C (10 mm Hg). (97.8% of theory). The product is colorless clear crystals of mp 50° C and $D_4^{20} = 1.9335$. Besides, 161g (97.5%) of sodium hydrogen sulfate was obtained.

EXAMPLE 13

Preparation of bromoacetic acid 94.5g (1 mol) of chloroacetic acid, 154.7g (1.3 mol) of potassium bromide, 127.5g (1.3 mol) of sulfuric acid and 100 ml of water were used and treated in a similar way with Example 12. Bromoacetic acid : 127g (98.5%). Sodium hydrogen sulfate : 175g (98.9%).

EXAMPLE 14

Preparation of bromoacetic acid 94.5g (1 mol) of chloroacetic acid, 142.8g (1.2 mol) of potassium bromide, 117.6g (1.2 mol) of sulfuric acid and 100 ml of water were used and treated in a similar way with Example 12. Bromoacetic acid : 135g (97.1%). Potassium hydrogen sulfate : 174g (98.3%).

EXAMPLE 15

Preparation of bromoacetic acid 47.7g (0.5 mol) of chloroacetic acid, 78.1g (0.65 mol) of potassium bromide and 50 ml of water were put into a 500 ml four necked flask, to which 65.7g (0.65 mol) of sulfuric acid was dropwise added, keeping the inert temperature below 55° C. The reaction mixture was heated at 100° ~ 125° C in an oil bath, blowing air into the mixture, which needed to complete removal of water. The resulted potassium hydrogen sulfate was filtered off and washed with acetone. The filtrate and washings were condensed to obtain crystals of bromoacetic acid (65.4g, 98.2%).

We claim:

1. A process for the preparation of bromoacetic acid esters which comprises gradually adding concentrated sulfuric acid to an aqueous solution of chloroacetic acid and an alkali metal bromide or ammonium bromide, maintaining the resulting mixture at a temperature of from about 40° C to about 70° C, adding to the reaction an organic solvent which is capable of forming an azeotrope, heating while removing water, and adding an alcohol and further heating, followed by isolating a bromoacetic acid ester from the resulting organic layer.

2. The process of claim 1, wherein the alkali metal bromide is sodium bromide or potassium bromide.

3. The process of claim 1, wherein the organic solvent is tetrachloroethylene, benzene, toluene or xylene.

4. The process of claim 1, wherein the alcohol is an aliphatic saturated alcohol, an aliphatic halogeno alcohol, an aliphatic nitro alcohol, an alicyclic alcohol, an aromaticsubstituted alcohol, a heterocyclic alcohol, or a glycol monoalkylether.

5. A process for the preparation of bromoacetic acid which comprises gradually adding concentrated sulfuric acid to an aqueous solution of chloroacetic acid and an alkali metal bromide or ammonium bromide while maintaining the temperature at from about 40° C to about 70° C, and thereafter heating the reaction mixture and removing water, to give bromoacetic acid.

6. The process of claim 5, wherein before heating the reaction mixture there is added an organic solvent which can form an azeotrope.

7. The process of claim 5, wherein while the reaction mixture is heated an inert gas is blown through it.

8. A process for the preparation of bromoacetic acid esters which comprises gradually adding concentrated sulfuric acid to an aqueous solution of chloroacetic acid and an alkali metal bromide or ammonium bromide, maintaining the mixture at a temperature of from about 40° C to about 70° C, then adding an alcohol and an organic solvent which is capable of forming an azeotrope and heating the mixture while removing water, and then isolating a bromoacetic acid ester from the resulting organic layer.

9. A process for the preparation of bromoacetic acid esters which comprises gradually adding concentrated sulfuric acid to a mixture of chloroacetic acid, an alkali metal bromide or ammonium bromide, an alcohol, water, and an organic solvent which is capable of forming an azeotrope, maintaining the mixture at a temperature of from about 40° C to about 70° C, heating to complete the reaction while removing water, and then isolating a bromoacetic acid ester from the resulting organic layer.

10. The process of claim 4, wherein the alcohol is hexyl alcohol, lauryl alcohol, ethylene glycol, 1,4-butandiol, glycerol, 2-chloropropanol, 1-chloro-3-bromo-2-methylpropanol, 2,3-dichloropropanol, 2-nitro-2-methylpropanol, cyclohexanol, 2-ethylcyclohexanol, cis-1,2-cyclohexandiol, 2-cyclohexanol, 2-chlorocyclohexanol, benzyl alcohol, p-methoxybenzyl alcohol, cinnamyl alcohol, p-chlorobenzyl alcohol, furfuryl alcohol, tetrahydrofurfuryl alcohol, ethylene glycol monobutylether or propylene glycol monoethylether.

* * * * *

UNITED STATES PATENT OFFICE
CERTIFICATE OF CORRECTION

Patent No. 4,123,443              Dated October 31, 1978

Inventor(s) Umekawa Osamu et al

It is certified that error appears in the above-identified patent and that said Letters Patent are hereby corrected as shown below:

Column 1, lines 5-6: "filed Sept. 9, 1976. BACKGROUND OF THE INVENTION" should read -- filed Sept. 9, 1976. --; line 28: "2,151,563" should read -- 2,151,565 --; line 30: "(1964." should read -- (1964)). --.

Column 3, line 25: "(land (2)" should read -- (1) and (2) --.

Column 6, line 60: "potassium" should read -- sodium --.

Column 7, line 22: "Sodium" should read -- Potassium --.

Column 8, line 4 of claim 4: "aromaticsubstituted" should read -- aromatic-substituted --.

Signed and Sealed this

Eighteenth Day of September 1979

[SEAL]

Attest:

LUTRELLE F. PARKER
Attesting Officer    Acting Commissioner of Patents and Trademarks